United States Patent
Soldatitsch et al.

(10) Patent No.: US 9,330,453 B2
(45) Date of Patent: May 3, 2016

(54) APPARATUS AND METHOD FOR DETERMINING A SKIN INFLAMMATION VALUE

(75) Inventors: Markus Soldatitsch, Weppersdorf (AT); Robert Strohal, Feldkirch (AT)

(73) Assignee: RED. SOFT IT-SERVICE GMBH, Weppersdorf (AT)

( * ) Notice: Subject to any disclaimer, the term of this patent is extended or adjusted under 35 U.S.C. 154(b) by 168 days.

(21) Appl. No.: 14/006,173

(22) PCT Filed: Mar. 20, 2012

(86) PCT No.: PCT/AT2012/000069
§ 371 (c)(1),
(2), (4) Date: Sep. 19, 2013

(87) PCT Pub. No.: WO2012/126027
PCT Pub. Date: Sep. 27, 2012

(65) Prior Publication Data
US 2014/0010423 A1    Jan. 9, 2014

(30) Foreign Application Priority Data
Mar. 24, 2011 (AT) ................................. A 420/2011

(51) Int. Cl.
*G06T 7/00* (2006.01)
*A61B 5/00* (2006.01)

(52) U.S. Cl.
CPC ............. *G06T 7/0012* (2013.01); *A61B 5/0064* (2013.01); *A61B 5/445* (2013.01)

(58) Field of Classification Search
None
See application file for complete search history.

(56) References Cited

U.S. PATENT DOCUMENTS

| | | | | |
|---|---|---|---|---|
| 5,588,428 A | * | 12/1996 | Smith | A61B 5/1077 382/128 |
| 6,081,612 A | * | 6/2000 | Gutkowicz-Krusin | A61B 5/0071 382/128 |
| 6,381,026 B1 | * | 4/2002 | Schiff | A61B 5/0059 356/601 |
| 6,413,212 B1 | * | 7/2002 | Raab | A61B 5/107 600/300 |
| 6,594,388 B1 | * | 7/2003 | Gindele | H04N 1/6027 358/520 |

(Continued)

FOREIGN PATENT DOCUMENTS

| | | |
|---|---|---|
| CN | 101282687 A | 10/2008 |
| CN | 101894212 A | 11/2010 |
| WO | 2010/044845 A1 | 4/2010 |

OTHER PUBLICATIONS

R. V. Dos Santos et al: "Beyond flat weals: validation of a three-dimensional imaging technology that will improve skin allergy research", Clinical and Experimental Dermatology, vol. 33, No. 6, pp. 772-775, Nov. 1, 2008.
Kim Min-Gi et al: "Objective interpretation of severity of SLS induced edema by stereoimaging", Journal of Dermatological Science, vol. 35, No. 2, pp. 125-131, Aug. 2004.

(Continued)

*Primary Examiner* — Tsung-Yin Tsai
(74) *Attorney, Agent, or Firm* — Jacobson Holman, PLLC

(57) ABSTRACT

The invention relates to an apparatus and to a method for determining a skin inflammation value. The apparatus comprises an optoelectronic measuring device, preferably a 3D scanner, for recording a three-dimensional image of an inflammation region on human or animal skin, wherein area-related, spatial, and color values of the three-dimensional image can be detected by the optoelectronic measuring device, a computing unit for calculating the skin inflammation value from the area-related, spatial, and color values detected by the measuring device, and a display unit for displaying the calculated skin inflammation value.

10 Claims, 10 Drawing Sheets

(56) References Cited

U.S. PATENT DOCUMENTS

| | | | |
|---|---|---|---|
| 6,757,413 B1 * | 6/2004 | LeMahieu | G06F 19/321 379/106.02 |
| 7,248,724 B2 | 7/2007 | Gutenev | |
| 7,495,208 B2 * | 2/2009 | Czarnek | A61B 5/0059 250/234 |
| 2004/0136597 A1 | 7/2004 | Hara et al. | |
| 2009/0137908 A1 | 5/2009 | Patwardhan | |
| 2010/0271470 A1 | 10/2010 | Stephan et al. | |

OTHER PUBLICATIONS

Piche E et al: "[FOITS (fast optical in vivo topometry of human skin): new approaches to 3-D surface structures of human skin].", Biomedizinische Technik, vol. 45, No. 11, pp. 317-322, Nov. 2000.

Westhauser M et al: "Optimizing color reproduction of a topometric measurement system for medical applications", Medical Engineering & Physics, vol. 30, No. 8, pp. 1065-1070, Oct. 1, 2008.

Chinese Office Action of Dec. 3, 2014 issued to a corresponding Chinese patent application.

Eurasian Office action of Nov. 14, 2014 issued to a corresponding Eurasian patent application.

* cited by examiner

APPARATUS AND METHOD FOR DETERMINING A SKIN INFLAMMATION VALUE

This is a national stage of PCT/AT12/000,069 filed Mar. 20, 2012 and published in German, which has a priority of Austria no. A 420/2011 filed Mar. 24, 2011, hereby incorporated by reference.

FIELD OF THE INVENTION

The invention relates to a device and a method for determining a skin inflammation score or value.

PRIOR ART

In the field of medicine, the most different diagnostic support devices are available to a physician. In this connection, X-ray apparatus, computer tomographs, various 3D scanners and many more have been used for long.

In the context of the diagnostic support for skin surface inflammations, only the first steps are being taken. In this respect, the article "Beyond flat weals: validation of a three-dimensional imaging technology that will improve skin allergy research" from the scientific magazine Clinical and Experimental Dermatology, Vol. 33, No. 6, Nov. 1, 2008 (2008-11-01), pp. 772-775, XP55030617 gives a description of a technique of how to measure the topography of the skin surface in the area of inflammations or skin weals by the aid of a 3D scanner. The thus produced high-resolution three-dimensional topographic image of the weal provides important additional clues to the diagnosing physician. That system and method, however, involve the disadvantage that only height and volume information can be included in the diagnosis. In the skin examination performed according to that article by a so-called prick test, this value or score will in fact be sufficient as a diagnostic support tool in most cases.

If, however, other types of skin examinations are performed (e.g. a so-called epicutaneous test), the sole height and volume scores will not suffice to provide sufficient diagnostic support to a diagnosing physician.

From Kim Min-Gi et al: "Objective interpretation of severity of SLS induced edema by stereoimaging.", Journal of Dermatological Science August 2004 LNKD-PUBMED: 15265524, Vol. 35, No. 2, August 2004 (2004-08), pp. 125-131 an alternative method for evaluating skin inflammations is known.

Piche E et al: "[FOITS (fast optical in vivo topometry of human skin): new approaches to 3-D surface structures of human skin].", Biomedizinische Technik. Biomedical Engineering November 2000 LNKD-PUBMED:11155533, Vol. 45, No. 11, November 2000 (2000-11), pp. 317-322 refers to an analysis of surface structures of human skin.

Westhauser M et al: "Optimizing color reproduction of a topometric measurement system for medical applications", Medical Engineering & Physics, Butterworth-Heinemann, GB, Vol. 30, No. 8, Oct. 1, 2008 (2008-10-01), pp. 1065-1070 aims at optimizing colored representations for medical applications.

From US 2004/0136579 A1 there has become known a method for supervising and quantification of the amount of red coloring of the wound of a patient, carrying out an evaluation on the basis of a determination of the brightness and/or color component in the RGB space for the determination of the boundary of a wound.

SUMMARY OF THE INVENTION

The object of the invention, therefore, resides in providing a diagnostic support tool for skin inflammations that is improved over the prior art. In addition to the space values, it is, in particular, intended to include also other diagnostically conclusive values on the measured inflammation region in the diagnostic support system.

For a device for determining a skin inflammation or dermatitis score or value, this is achieved by an optoelectronic measuring instrument or device, preferably a 3D scanner, for taking a three-dimensional image of an inflammation area on human or animal skin, wherein area-related, space and color values of the three-dimensional image are detectable by the optoelectronic measuring instrument, a processing or computing unit for calculating the skin inflammation score from the area-related, space and color values detected by the measuring instrument, and a display unit for displaying the calculated skin inflammation score, being essentially characterized in that the processing unit distinguishes the area-related values of the scanned three-dimensional image into an inflammation focus and a focus-surrounding area adjoining and surrounding the inflammation focus by delimiting the color values of the individual pixels and by delimiting the space values of the individual pixels and in that each color value corresponds to a magenta value in the CMYK color model. Consequently, not only space values will be included in the skin inflammation score or value to be determined, but also the area-related and color values of the scanned inflammation area will be additionally taken into account. In other words, the present invention enables the determination of a diagnostically much more conclusive score, which comes closer to the actual severity of the inflammation. The diagnosis will thus be substantially supported and improved, and physicians will no longer have to make diagnoses merely based on their subjective assessments of roughness, size and redness, but will be able to make a more objective diagnosis based on stored empirical values of previous measurements and the values actually measured and comparable to the experimental values.

Basically, it is possible to regard the total scanned area as an inflammation area to be uniformly assessed. According to the invention, it is, however, provided that the processing unit distinguishes the area-related values of the scanned three-dimensional image into an inflammation focus and an area adjoining and surrounding the inflammation focus by delimiting the color values of the individual pixels or by delimiting the space values of the individual pixels. For the distinction between the inflammation focus and the focus-surrounding area, a combination of the color values, space values and/or area-related values can, of course, also be applied. The CMYK color model is a so-called subtractive color model, wherein CMYK stands for cyan, magenta, yellow and key.

According to a preferred exemplary embodiment of the invention, it may be provided that the scanned three-dimensional image of the inflammation area is comprised of a multitude of pixels arranged in a three-dimensional coordinate system in grid-like fashion, wherein each area-related value corresponds to a single pixel that is unique in the coordinate system. The pixels formed in the coordinate system thus provide a virtual image of the real skin surface. In a preferred manner, it may be provided that each space value corresponds to a height value of the respective pixel in the three-dimensional coordinate system.

In order to obtain as convincing a result as possible, it is preferably provided that both a, preferably single, color value and a, preferably single, space value are assignable to each area-related value of a three-dimensional image scanned by the optoelectronic measuring instrument. A single pixel or picture point can preferably have a dimension ranging between 1 µm and 10 µm. In a particularly preferred manner, the pixel size is exactly 3.05597 µm.

The HSV color space is the color space of some color models, in which the color hue, the color saturation and the lightness or darkness value are applied.

The present invention in the first place serves the diagnostic support in dermatitis, i.e. an inflammatory reaction of the skin, above all the sclera (dermis). The term eczema can be also used as a synonym for dermatitis. The skin inflammations to be examined may comprise both naturally occurring inflammations and those deliberately induced by allergy tests (e.g. an epicutaneous test or a prick test). Yet, also moles or wounds can be assessed, to which end the classification method will, however, have to be adapted accordingly.

In order to obtain convincing detailed values of the delimited areas, which apply to the whole delimited area, it may preferably be provided that a relative overall color value of the entire inflammation focus is determinable by comparing the averaged color values in the inflammation focus and the averaged color values in the focus-surrounding area. Further options are that an absolute overall volume value of the entire inflammation focus is determinable from the space values in the inflammation focus, and that a relative overall volume value of the inflammation focus is determinable by comparing averaged space values in the inflammation focus to averaged space values in the focus-surrounding area.

Especially for said relative overall volume value, it may preferably be provided that the relative overall volume value is a comparative value of the surface roughness in the inflammation focus to the surface roughness in the focus-surrounding area. In this case, the calculation method of the surface roughness may be guided by the calculation of the line roughness according to the German Industrial Standard EN ISO 4288.

Further additional or alternative detailed values that can be used to calculate the overall skin inflammation score will be indicated below. It may, for instance, be provided that an area-related value corresponds to a peripheral value corresponding to the periphery of the inflammation focus, and/or an area-related value corresponds to an area value representing the surface area of the inflammation focus. Furthermore, it may be provided that an area-related value is formed as a function of the area value and the peripheral value and corresponds to a compactness value representing the ratio of the peripheral value to the area value, or that an overall volume value corresponds to an average height value representing the average height of all elevations in the inflammation focus and/or a maximum-height area value representing the surface area of the highest elevations, the highest elevations being those elevations whose heights are at least 70%, preferably at least 85%, of the height of the highermost elevation.

Protection is, moreover, sought for a method of determining a skin inflammation score or value, which can, in particular, be performed using a device according to the invention or a preferred embodiment thereof, comprising an optoelectronic measuring instrument or device, preferably a 3D scanner, a processing or computing unit, and a display unit, characterized by the steps: taking a three-dimensional image of an inflammation area on human or animal skin by the optoelectronic measuring instrument, determining area-related, color and space values of the three-dimensional image, calculating the skin inflammation score from the calculated area-related, color and space values, subdividing the inflammation area into an inflammation focus and a focus-surrounding area, wherein the area of the inflammation focus is delimited from the area of the focus-surrounding area by the color and/or space values assigned to the individual area-related values and displaying the calculated skin inflammation score on the display unit. This method is thus not to be regarded as a diagnosing method, but as a data-detecting or data-processing method (color, space and area-related values) to be used in a diagnosing method performed by a physician.

Further preferred method steps are additionally defined in claim 14. In this context, it should be noted that the characteristic features of claim 14 more clearly describe and define the steps of determining the three-dimensional image and calculating the skin inflammation score.

SHORT DESCRIPTION OF THE DRAWINGS

In the following, further details and advantages of the present invention will be explained in more detail by way of the description of the Figures with reference to the exemplary embodiments illustrated in the drawings. Therein:

Figure 6:
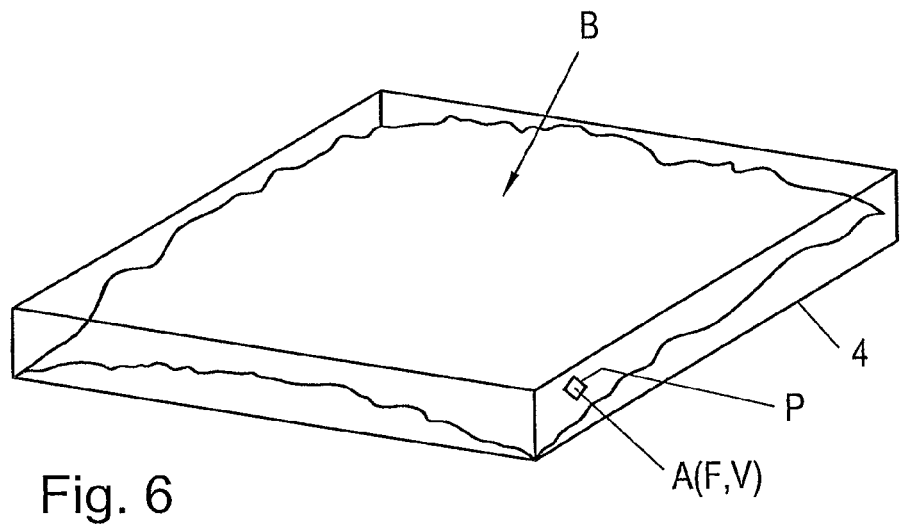
Figure 7:
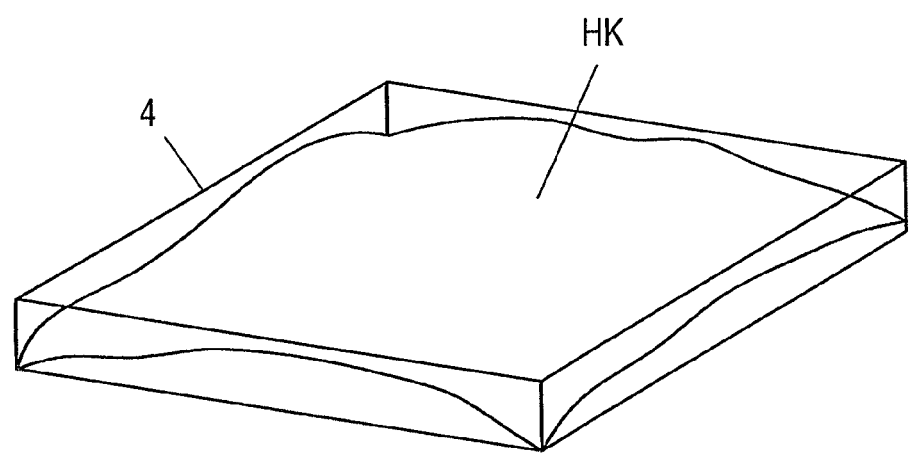
Figure 8:
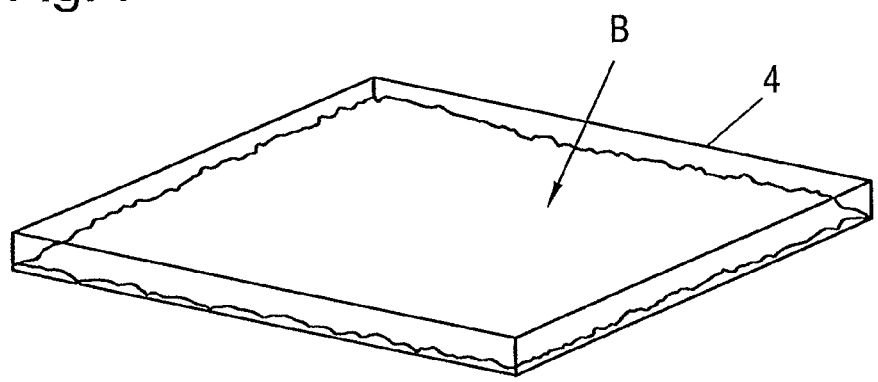
Figure 9:
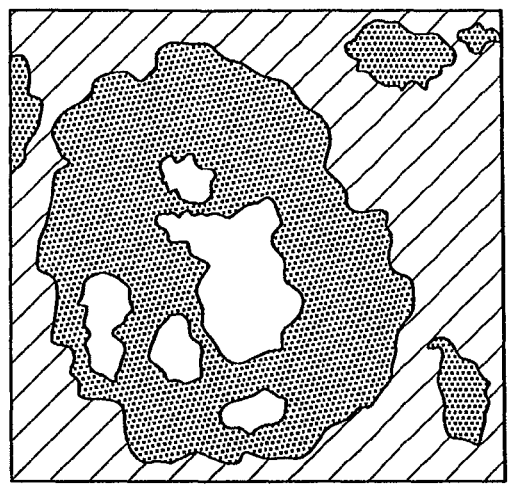
Figure 10:
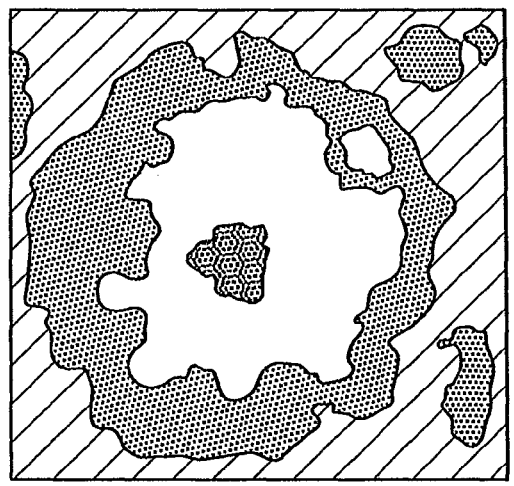
Figure 11:
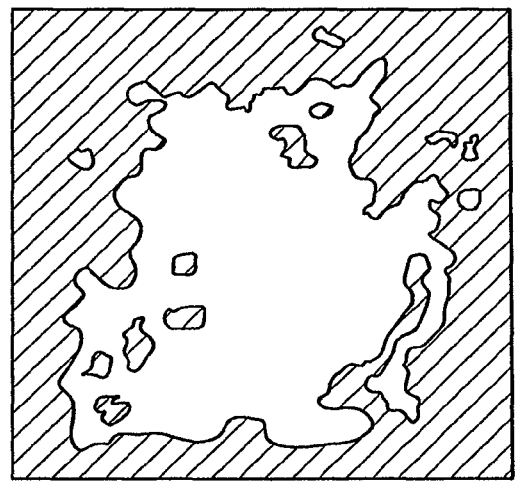
Figure 12:
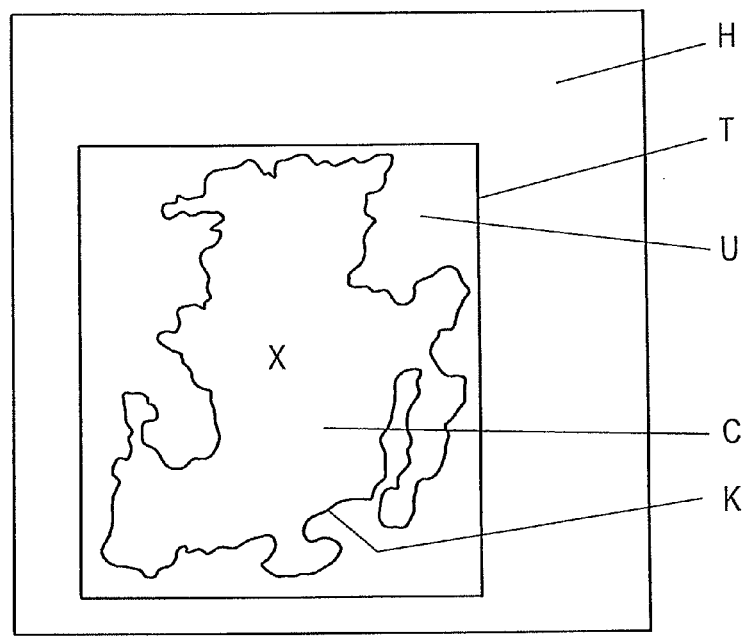
Figure 13:
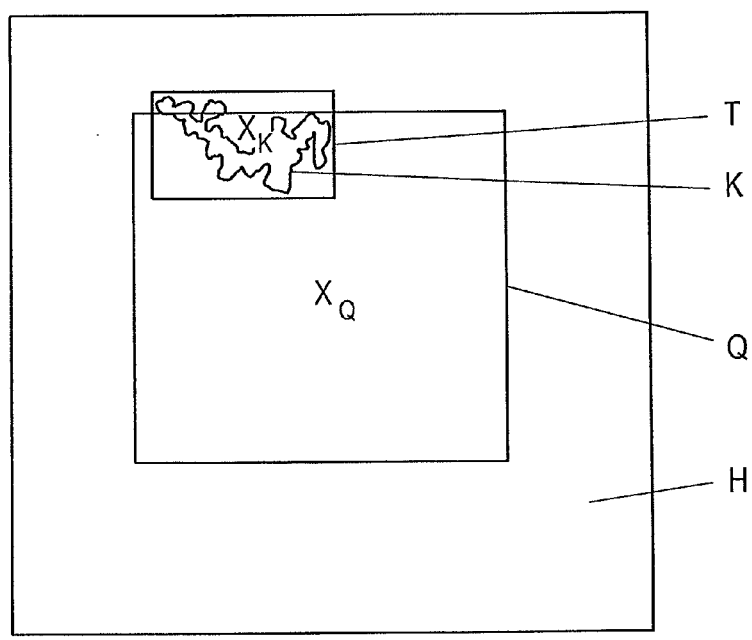
Figure 14:
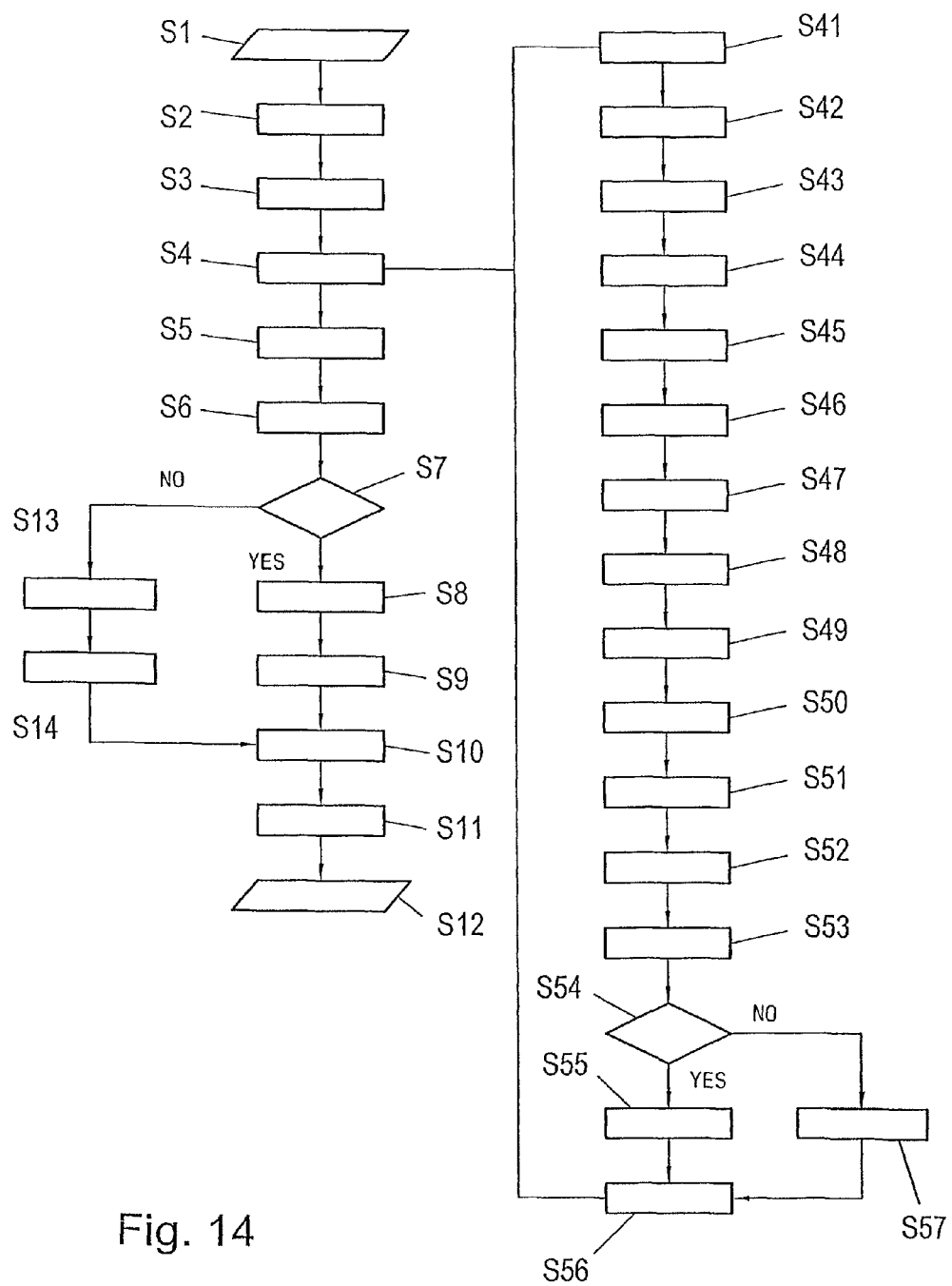
Figure 15:
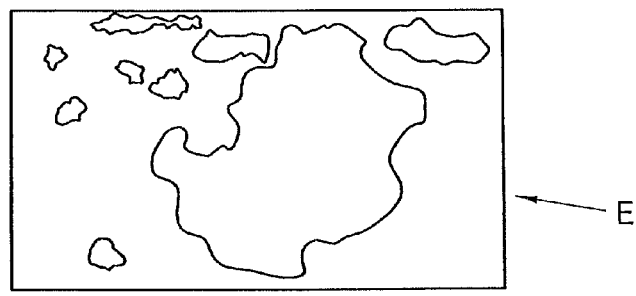
Figure 16:
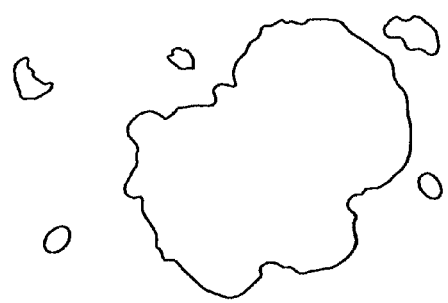
Figure 17:
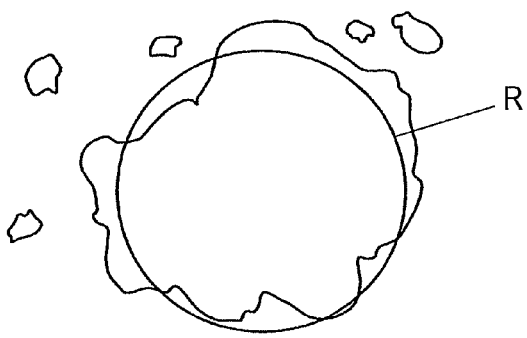
Figure 18:
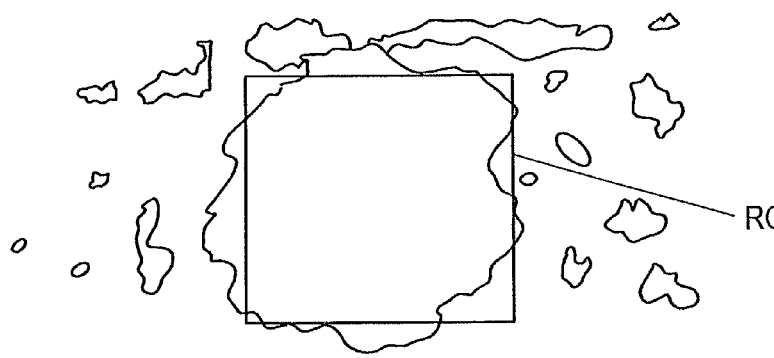
Figure 23:
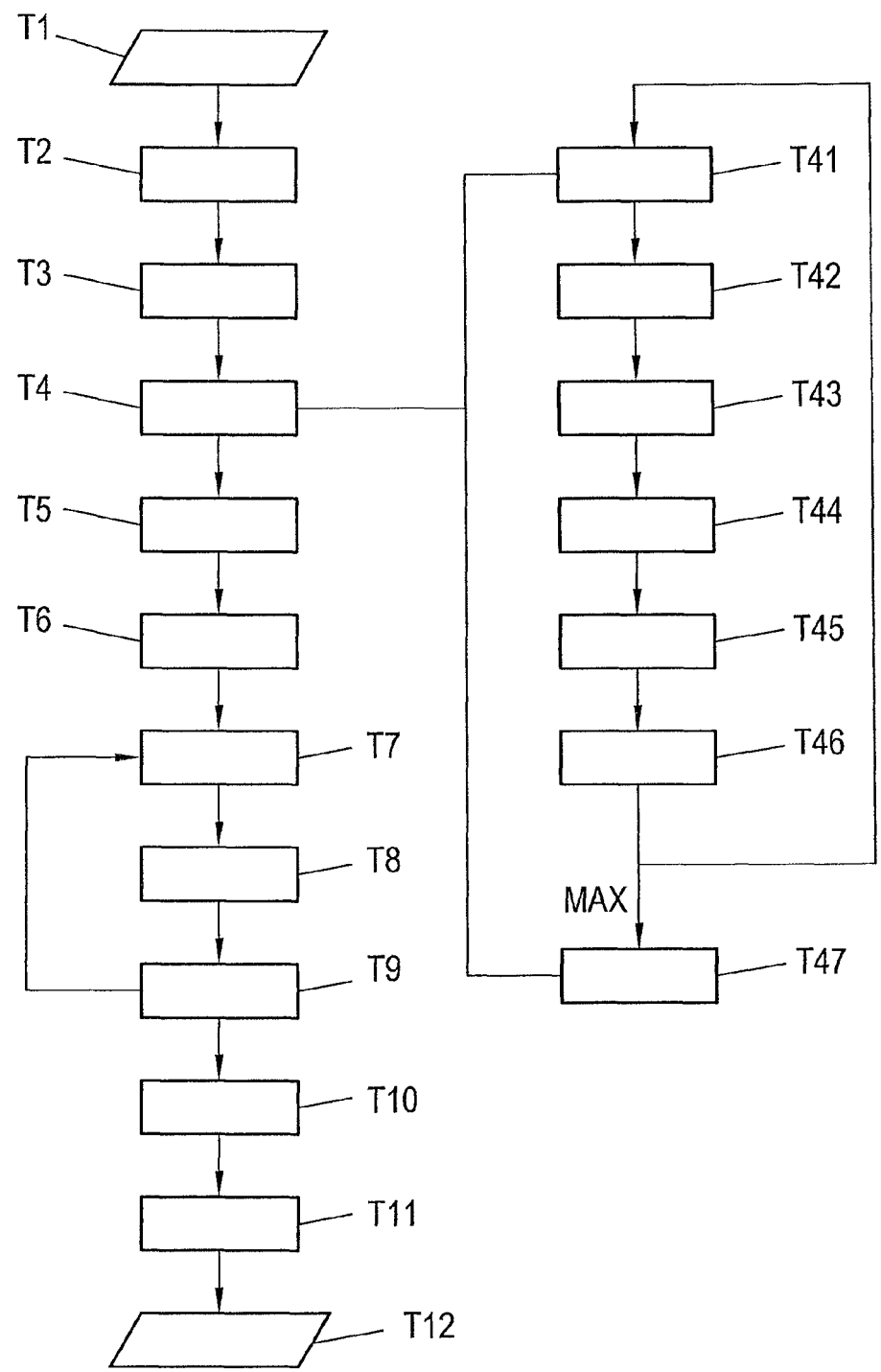

FIGS. 6 to 8 indicate the procedure of smoothing a height image, illustrated in the three-dimensional coordinate system;

FIGS. 9 and 10 illustrate the heights in a grey value image;

FIG. 11 is a binary image of the average heights;

FIG. 12 is an image with a height boundary contour;

FIG. 13 is an image examining the center of gravity of the height boundary contour;

FIG. 14 is a flow chart of a first method for determining a skin inflammation score;

FIGS. 15 to 18 illustrate the realization of a contour calculation based on color and area-related values;

FIGS. 19 to 22 depict the value calculating steps in a second method for determining a skin inflammation score; and FIG. 23 is a flow chart indicating the most important the second exemplary method for determining a skin inflammation score.

DETAILED DESCRIPTION OF PREFERRED EMBODIMENTS

Figure 1:
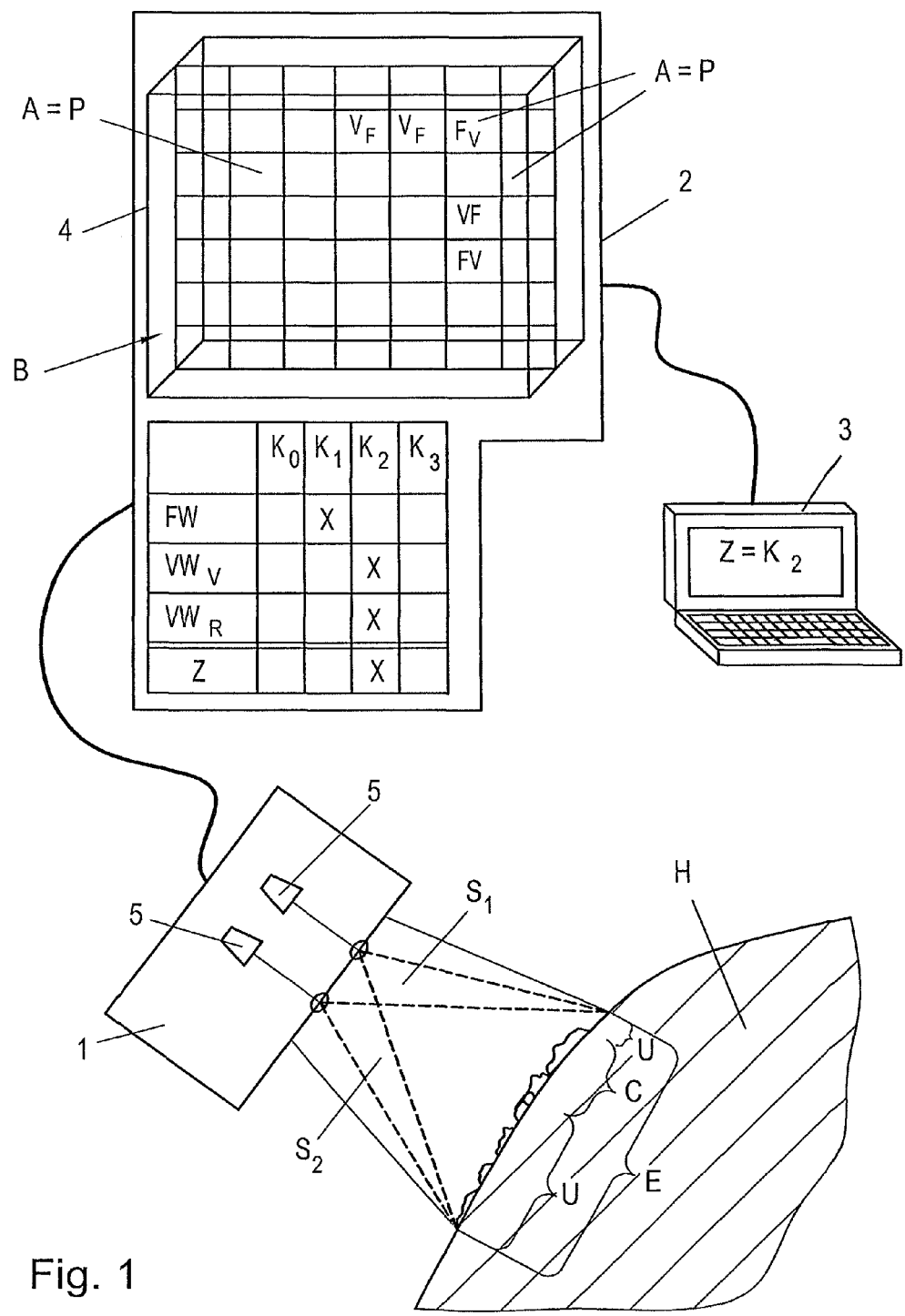
FIG. 1 is a schematic illustration of a device for determining a skin inflammation score or value.

FIG. 1 depicts the essential components of a device for determining a skin inflammation score Z. To this end, an optoelectronic measuring instrument or device 1 (3D scanner—e.g. PRIMOS pico by GFM) is held above, or preferably directly placed on, the skin H of a human or animal. The measuring instrument 1 should, of course, be used above a (suspected) inflammation area E. By the individual scanning elements 5, the whole inflammation area E is detected via two scan areas $S_1$ and $S_2$ and a corresponding three-dimensional image B is transmitted to the processing or computing unit 2. Said image B consists of a multitude of pixels P each corresponding to an area-related value A. Each individual area-related value A is kind of filled with a color value F and a space value V. The whole image B is plotted in a three-dimensional coordinate system 4 (cf. also FIG. 6). The processing unit 2 may be configured as a computer that is connected to the measuring instrument 1. The processing unit 2 may, however, also be directly integrated in the measuring instrument 1.

By way of the gathered values A, V and F, the inflammation area E is then subdivided into an inflammation focus C and a focus-surrounding area U in a first important calculation step. After this, absolute color values FW and/or absolute volume values VW for the inflammation focus C, and/or relative color values FW and/or relative volume values $VW_R$ over the entire inflammation area, are determined. The relative color value FW can, for instance, be calculated by subtracting or dividing the averaged magenta value of the focus-surrounding area U from or by the averaged magenta value of the inflammation area C. The overall volume value VW as an absolute volume value $VW_V$ may, for instance, represent the concrete overall volume of the whole weal or inflammation. The reference letter $VW_R$ may represent a relative overall volume value in which the roughnesses of the inflammation focus C and the focus-surrounding area U are compared.

Subsequently, each of these determined values FW, $VW_V$ and $VW_R$ can be classified into one of the inflammation classes $K_0$, $K_1$, $K_2$ or $K_3$. The limits of these classification classes are predefined, based on empirical values stored, collected and pre-categorized in the processing unit 2. The assignment to the individual classes $K_0$, $K_1$, $K_2$ or $K_3$ will result in an averaged, preferably rounded, skin inflammation score Z, which will then be accordingly output on the display unit 3. A merely acoustic output via a loudspeaker can also be used equivalently to the optical display. The display unit 3 may also comprise individual light diodes. The skin inflammation score may, for instance, be identified by the color of a diode. Yet, also the number of light-emitting diodes may reflect the skin inflammation score.

Figure 3:
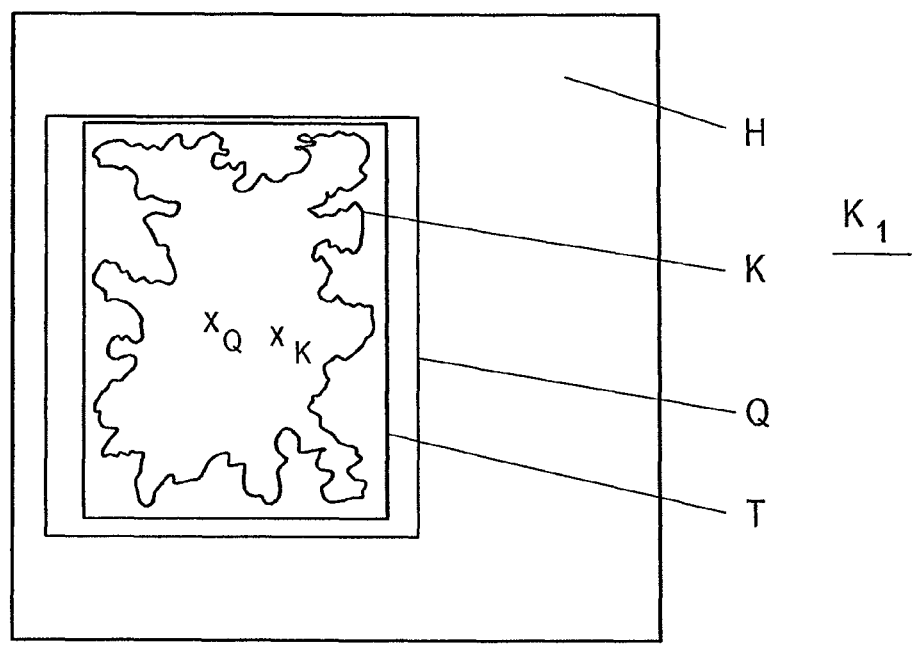
Figure 4:
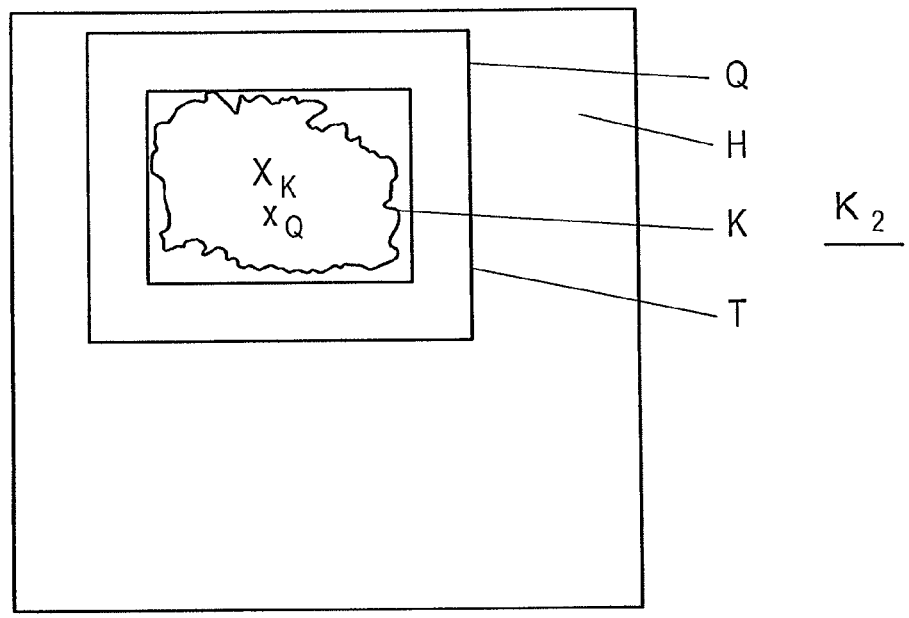
Figure 5:
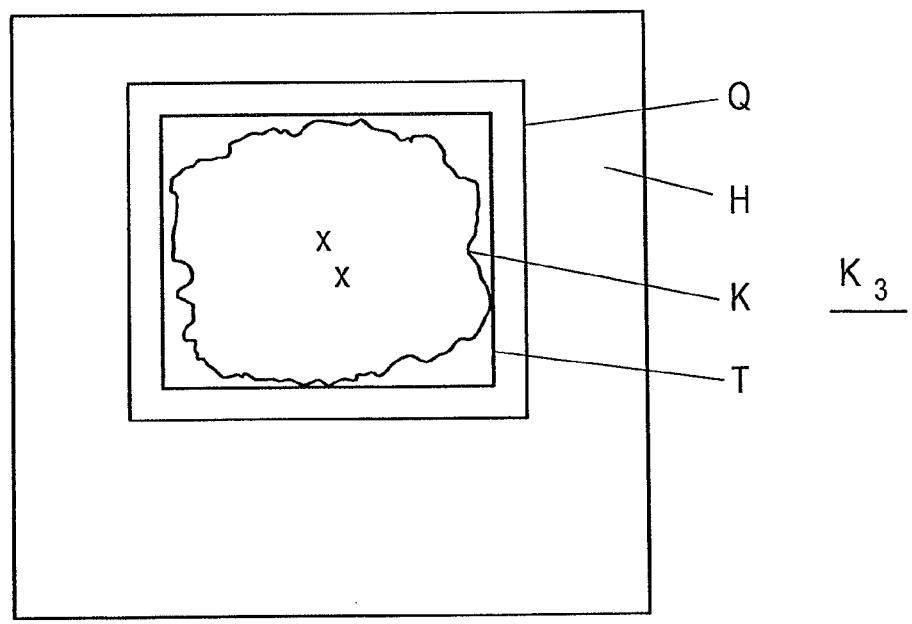

FIGS. 2 to 5 depict exemplary images of different inflammation areas E, wherein a segmenting square Q and a contour-surrounding rectangle T are each entered. The contour K constitutes the border between the inflammation focus C and the focus-surrounding area U. In addition, the center $X_Q$ of the segmenting rectangle Q and the center of gravity $X_K$ of the contour K are illustrated in each of FIGS. 2 to 5. The intersection of the letter X is to be regarded as the respective exact point. FIG. 5 depicts an intense redness and swelling with large blisters (inflammation class $K_3$), in which the left-hand upper X corresponds to the center of the segmenting rectangle Q and the right-hand lower X corresponds to the center of gravity of the contour K.

In the following, two methods of determining a skin inflammation score are described in detail, wherein it is, however, not to be excluded that individual or several of the calculation steps of the two methods are also carried out in a separate method including arbitrarily "mixed" calculating steps. It goes without saying that methods steps may also be partially omitted from each method. What is essential for the calculation of the skin inflammation score is that the respective area-related, space and color values A, V and F of the three-dimensional image B scanned by the optoelectronic measuring instrument be taken into account. Nor is it, of course, to be excluded that even other alternative calculation variants not mentioned herein may be used to determine a skin inflammation score Z.

Correspondingly, a first method using exemplary algorithms for an epicutaneous test will be described below. The analysis of the epicutaneous test is subdivided into three steps:
i) Recognizing the urtica (weal) by means of a height segmenting method
ii) Measuring the urtica (height and color values)
iii) Evaluating the measured results These three steps will be described below, wherein the problems of the hitherto used solution will be outlined and options how a new software solution suitable for the invention will even better and more efficiently assist procedures in a physician's practice will be offered.

By newly implementing the software solution, existing problems can be avoided beforehand and the structure of the application can be optimally adapted to current requirements. Furthermore, there is the chance to perform optimizations in the individual fields and thereby render the overall support process more efficient, while reducing the time required by the users of the system.

i) Height-Segmenting

The segmentation is roughly subdivided into 7 steps:
1. Smoothing of the height image
2. Filtering of the height image
3. Representation of the heights in a grey value image (the maximum height being white, the minimum height being black)
4. Determination of the above-average magenta values in the CMYK image and increase of the values in the height grey-value image in those points which have above-average magenta values
5. Calculation of the average height and creation of a binary image
6. Tracing of the boundary contour of the largest continuous elevation
7. Verification whether the center of gravity of the height grey-value image is located within the rectangle encompassing the traced boundary contour of the largest continuous elevation.

1. Smoothing of the Height Image:

Since the detected skin site (cf. original height image according to FIG. 6) in most cases would comprise a curvature, the height image is largely straightened to enable further operation with an idealized, plane skin.

To this end, the 25 outermost height values on the edges are each used to calculate a curved plane that corresponds to the skin curvature HK (cf. FIG. 7).

The new height image is then formed as follows: The values that are smaller in the original height image than the corresponding value of the calculated plane are set on the value of the calculated plane. All other values retain their original values. Subsequently, the corresponding value of the calculated plane is subtracted from each height value. In this manner, the curvature of the skin and possible skin pores generating deeper valleys in the height image are eliminated. The height 0 can then be taken as the basic height of the skin. Such a smoothed height image (original height image minus calculated skin curvature) is illustrated in FIG. 8.

2. Filtering of the Height Image:

In order to eliminate smaller aberrations from the height image, the latter is smoothed by the aid of a median filter (currently it is operated with the exponential neighborhood 3).

3. Height Representation in a Grey Value Image (FIG. 9):

For the further processing of the height image by the aid of image processing algorithms, a grey value image with 256 grey shades is calculated from the height image. The highest height is used for the value 255 (white), the lowest height is used for the value 0 (black). The height values in between are proportionally calculated into different grey shades.

4. Increase of the Values in the Height Grey-Value Image on Those Sites which have Above-Average Magenta Values (FIG. 10).

In order enable a better limitation of the site picturing an inflammation, these are increased in the height image by the degree of the above-average redness. To this end, the original image is converted into a CMYK image and the magenta channel is considered. A grey value image corresponding to the magenta channel is established, yet all magenta values that do not reach a given percentage (e.g. 120%) of the average magenta value are will be set to zero.

After this, the individual points of the height image are considered and compared to the respective pixel in the magenta image. If the value in the magenta image is higher than that in the grey value image of the height image, the pixel in the grey value image of the height image will be newly calculated from a portion of the current value and a portion of the value of the magenta image (for instance, the value of the magenta image contributes 60%, and the value of the height grey-value image contributes 40%, to the new value).

5. Calculation of the Average Height and Creation of a Binary Image (FIG. 11):

From the grey value image of the height image amplified by the aid of the magenta channel of the CMYK image, a binary image is then calculated, which is necessary for the search of contours. In doing so, the average grey value (multiplied by a coefficient, currently 2.0) is adopted as a threshold.

Before the binary image is created, the grey value image is smoothed by a median filter (the current neighborhood being 9). And the binary image is eroded and dilated (currently, three iterations of eroding and one iteration of dilating are performed).

6. Tracing of the Boundary Contour of the Largest Continuous Elevation (FIG. 12):

Those parts of the height image which lie above the average height (multiplied by a coefficient) are imaged as white spots in this binary image. The algorithm then searches the white spot with the largest surface area in the binary image and provides the boundary contour K of the area as well as a boundary rectangle T encompassing the contour K. The area encompassed by the contour K (inflammation focus C) captures that part in the height image which represents the highest cohesive inflammatory elevation, and hence the searched skin swelling, and is surrounded by the focus-surrounding area U.

7. Calculation and Verification of the Center of Gravity of the Height Grey-Value Image (FIG. 13):

As a control measure, the center of gravity of the height grey-value image is calculated (point $X_Q$). If the center of gravity lies within the area of the traced boundary contour K, or the rectangle T encompassing said contour K, this will confirm the traced contour K, and hence the localization of the supposed measuring area.

Unless the center of gravity is disposed within the rectangle T as in FIG. 13, it can be anticipated that the traced elevation is not prominent relative to other elevations. As a rule, this will comprise those tests which show no or a below-average swelling.

In this case, the further measurement is not based on the area encompassing the contour K, but on the area of the supposed measuring area, or the square Q encompassing said area. The center $X_Q$ of the square Q is represented by the center of gravity of the height grey-value image (the size of the square corresponding to the respective real measuring area).

ii) Measuring:

After having completed the identification of the skin swelling, the latter is measured. In doing so, three characteristic values are determined, which are used for the assessment:

1. The volume of the swelling in relation to the surface area of the swelling
2. The roughness of the swelling in relation to the roughness of the remaining skin surface
3. The redness of the swelling in relation to the remaining skin color 1. The Volume of the Swelling in Relation to the Surface Area of the Swelling:

The base of the swelling is that area which is encompassed by the contour K. The overall volume of the swelling located within the contour K is then calculated. In doing so, only that portion of the height which lies above the average height of the skin is counted.

This calculated overall volume of the swelling is divided by the surface area. The result is the average height of the swelling. This is used for the assessment.

2. The Roughness of the Swelling in Relation to the Roughness of the Remaining Skin Surface:

A further significant characteristic of the swelling is its roughness. In order that a potentially rough normal skin will not excessively influence the measuring results, the roughness inside and outside the rectangle encompassing the boundary contour is calculated. The roughness of the swelling (inside the rectangle) minus the roughness of the remaining skin (outside the rectangle) will then be used for the assessment.

The method implemented for calculating the surface roughness is based on the method for calculating the line roughness (DIN EN ISO 4288).

As boundary parameters, 10% and 90% are respectively used. This means that the difference between the average heights resulting in a surface area material portion of 10% and 90%, respectively, is used as a roughness value rather than the difference between the highest point (0% surface area material portion) and the lowest point (100% surface area material portion).

3. The Redness of the Swelling in Relation to the Remaining Skin Color:

In addition to the two measuring values calculated from the height image, the degree of redness of the measuring area is determined from the color image. To this end, the magenta channel of the CMYK representation of the original color image of the measuring site is used.

Similarly, as in the calculations of the roughness and the average volume, a value inside and a value outside the area delimited by the contour are also calculated in this case. For further assessment, the average value inside the contour minus the average value outside the contour is used.

iii) Assessment:

After having been measured, the urtica is assessed and categorized into one of the four classes usual in practice. The Table below contains a broad, subjective description of the classes.

Figure 2:
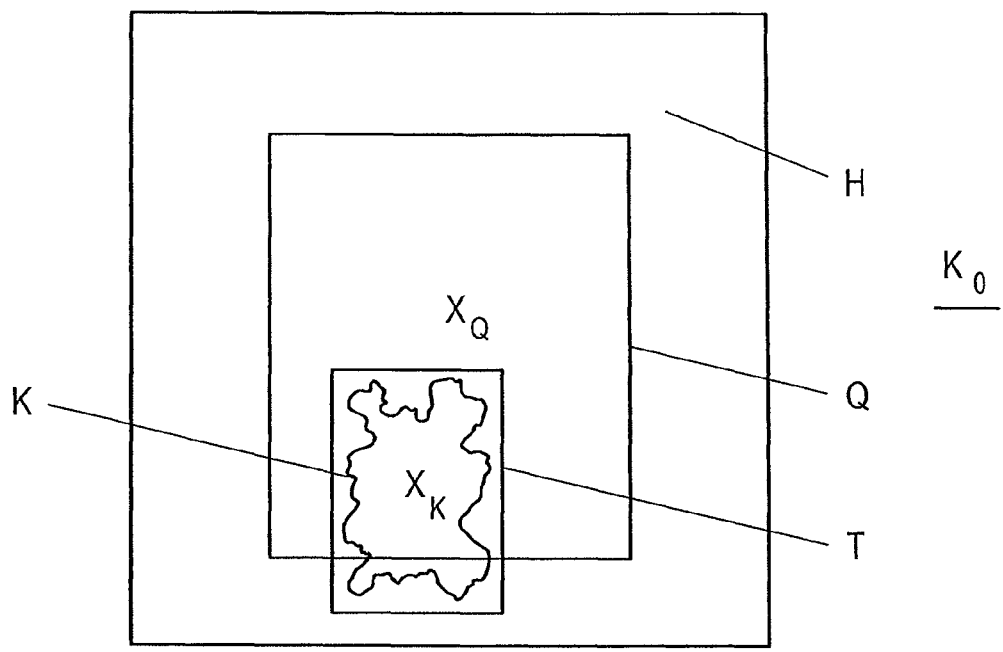
FIGS. 2 to 5 are pictures of skin inflammation areas showing the four different classes of skin inflammation scores.

| Class | Example | Description |
| --- | --- | --- |
| 0 ($K_0$) | FIG. 2 | Doubtful reaction: possibly slight redness |
| 0 ($K_1$) | FIG. 3 | Weakly positive reaction: red and slightly swollen skin |
| 0 ($K_2$) | FIG. 4 | Strongly positive reaction: red and swollen skin with a few blisters |
| 0 ($K_3$) | FIG. 5 | Extremely positive reaction: intense redness and swelling with large blisters |

The overall assessment of the urtica is composed of the individual partial evaluations of the characteristic values derived from measuring. In the present case, three partial evaluations in four classes are performed, whose rounded mean values yield the class of the overall assessment. Since the significance of the redness value decreases with a strongly reddened normal skin, this circumstance is explicitly taken into account for the assessment.

If a skin redness of the normal skin above the limit value is detected, the redness of the swelling will not be used for the assessment.

The following exemplary sample calculation will serve better understanding:

|  | Example class limits | Example measuring values | Partial evaluation classes |
|---|---|---|---|
| Volume | 0-5, 5-11, 11-16, 16-infinite | 6 | 1 |
| Roughness | 0-3, 3-13, 13-17, 17-infinite | 14 | 2 |
| Redness between 0 and 1 | 0-4, 4-9, 9-11, 11-infinite | 2 | 3 |

From this results an overall assessment of 2 (the mean value of 1+2+3 being 2).

Sample calculation with strong skin redness:

|  | Example class limits | Example measuring values | Partial evaluation classes |
|---|---|---|---|
| Volume | 0-5, 5-11, 11-16, 16-infinite | 19 | 3 |
| Roughness | 0-3, 3-13, 13-17, 17-infinite | 18 | 3 |
| Redness between 0 and 1 | 0-4, 4-9, 9-11, 11-infinite | 2 | 1 |

The classification of the redness would lower the overall result to 2 (the rounded mean value of 3+3+1 being 2). By taking into account the skin redness above the limit value, a classification of 3 results (the mean value of 3+3 being 3).

FIG. 14 illustrates a flow chart of the first method, again outlining the above-mentioned method steps in a logical context.

In order to not only indicate general ranges for the inflammation classes $K_0$ to $K_3$, four concrete Examples of measuring values plus assessment pertaining to different classes are indicated below. They are concretely related to the different degrees or classes of inflammations represented in FIGS. 2 to 5.

i) Measuring

The following characteristic values were determined in respect to these images:
1. Average height (average volume) of the inflammation
2. Roughness value minus basic roughness (relative roughness)
3. Redness in relation to the color of the remaining skin (relative redness).

If the center of gravity $X_Q$ of the segmenting image is not located in the rectangle T surrounding the contour K, the area inside or outside the square Q formed with the center of gravity $X_Q$ of the segmenting image as its center is used for measuring rather than the areas inside or outside the contour K and inside or outside the rectangle T encompassing the contour K.

1. Average Height (Average Volume) of the Inflammation

The heights of all measuring points located within the identified urtica that is limited by the contour K are summed up. In doing so, only that portion of the height is counted which lies above the average height of the skin. This volume is divided by the number of measuring points. The thus calculated average volume is used for the assessment.

Values of the example images (the area of a pixel is 0.00305597 mm$^2$):

|  | Overall volume of urtica | Overall surface area of urtica | Average volume per pixel |
|---|---|---|---|
| FIG. 2 - $K_0$ | 1.6913977 mm$^3$ | 190.9985264 mm$^2$ | 0.0000271 mm$^3$ |
| FIG. 3 - $K_1$ | 7.3151578 mm$^3$ | 61.7780914 mm$^2$ | 0.0003619 mm$^3$ |
| FIG. 4 - $K_2$ | 16.6766525 mm$^3$ | 62.867547 mm$^2$ | 0.0008106 mm$^3$ |
| FIG. 5 - $K_3$ | 40.2830175 mm$^3$ | 93.6228937 mm$^2$ | 0.0013149 mm$^3$ |

2. Roughness Value Minus Basic Roughness (Relative Roughness):

The roughness of the surface is calculated for the surface area inside the contour K and for the surface area between the contour K and the rectangle T. The difference between the two roughness values forms an assessment basis.

Values of the Example Images:

|  | Roughness inside boundary rectangle | Roughness outside boundary rectangle | Difference |
|---|---|---|---|
| FIG. 2 - $K_0$ | 0.0732433 mm | 0.0550084 mm | 0.0182349 mm |
| FIG. 3 - $K_1$ | 0.1658371 mm | 0.0924609 mm | 0.0733762 mm |
| FIG. 4 - $K_2$ | 0.3263570 mm | 0.1401592 mm | 0.1861978 mm |
| FIG. 5 - $K_3$ | 0.4609349 mm | 0.1506546 mm | 0.3102803 mm |

3. Redness in Relation to the Color of the Remaining Skin (Relative Redness):

The average redness of the areas inside and outside the identified urtica (contour K) is determined from the magenta channel of the color image. The difference of the two average values enters into the assessment.

Values of the Example Images:

|  | Redness of urtica | Redness of the surroundings | Difference |
|---|---|---|---|
| FIG. 2 - $K_0$ | 65.104384 | 66.6805231 | −1.5761391 |
| FIG. 3 - $K_1$ | 75.2352490 | 67.1557576 | 8.0794914 |
| FIG. 4 - $K_2$ | 137.7521633 | 107.7737394 | 29.9784239 |
| FIG. 5 - $K_3$ | 104.6286619 | 67.2027139 | 37.425948 |

3a. Redness of the Surrounding Skin

If the average value of the redness of the skin outside the urtica exceeds a threshold value, the relative redness will not be used for the assessment.

Values of the Example Images:

Class 0: 66.6805231

Class 1: 67.1557576

Class 2: 107.7737394

Class 3: 67.2027139 ii) Assessment:

The assessment is initially performed separately for each value. To this end, a limit value is fixed for each measuring value. The presently used limit values (which may, however, be fixed and changed individually upon consultation with physicians) for the individual measuring values are as follows:

|  | Class 0 | Class 1 | Class 2 | Class 3 |
| --- | --- | --- | --- | --- |
| Average volume of inflammation | <0.000225492 | <0.000646506 | <0.001029246 | >=0.001029246 |
| Roughness value minus basic roughness | <0.02655275 | <0.1102376 | <0.21623841 | >=0.21623841 |
| Redness in relation to color of remaining skin | <4.68131157 | <12.48887981 | <32.98374644 | >=32.98374644 |

There is an additional threshold value, which defines from which redness onwards the surrounding skin is regarded as too reddish, and which determines whether said redness, based on the color of the remaining skin, can be used for the assessment. This threshold value at present is fixed at 109.98770675.

The overall classification results from the (rounded) average classification of the partial evaluations.

In the following, a second variant for determining a skin inflammation score Z is indicated, which can be performed by the device according to the invention.

By analyzing various color spaces and representations, it was found that the magenta color space in the CMYK false-color representation and the saturation value in the HSV color space were best suited for filtering and assessing inflammation focuses on human skin. At the beginning of the image processing, two images from the original image (FIG. 15) are therefore generated, followed by a conversion into a CMYK and a HSV picture.

The next step may optionally comprise a pre-filtering of the image to filter out plasters. In doing so, it is differentiated for each pixel, based on a fixed limit value in the magenta plane of the CMYK image, whether the picture point corresponds to a plaster or to the skin (=so-called threshold function). As a starting value, the limit value is assumed to be 100, which means that, when passing through each pixel of the image, it is verified whether the magenta value is higher than 100 or not. If so, the pixel value is taken over from the original image; if not, the color value is set to zero (=black). After this, it is verified by an evaluation function whether sufficient picture points have been left for further processing or whether the threshold has been set too high. In the latter case, a reduction of the fixed limit value is effected, and filtering and verifying are started anew. This process is repeated up to four times in order to ensure that optimum filtering of plaster segments from the image takes place without loosing too much of the actual information.

Then, the image is filtered in the magenta color space. To do this, two variants are available, which will be used as a function of the employed camera. In the first variant, the magenta mean value of all obtained pixels is calculated. After this, it is again filtered out in a loop by means of a threshold function (mulfactor), whether a picture point can be assigned to an inflammation or to neutral skin. In doing so, the threshold value is iteratively reduced, i.e. in the first step all pixels that are above a defined percentage of the average magenta value are taken over. In the second variant, a mean value from the 5×5 pixel environment of the pixel is compared to the threshold value rather than comparing the pixel value proper with the average magentavalue*mulfactor. The resultant image is in both cases a grey value image including the filtered magenta pixels. Subsequently, several image processing steps are performed in order to optimize the filtering result. They comprise a mean value filter (to eliminate pixel noise, i.e. small pixel groups are filtered out). Eroding and dilating functions are further used to close possible gaps. This is followed by a conversion into a binary image (=black/white picture) in which a contour finding algorithm is carried out. The traced contours are examined step by step in order to enable the identification of a so-called region of interest ROI as a potential segmentation area (cf. FIG. 16). To this end, the compactness of the contour (=surface area of the contour/periphery of the contour) will be initially calculated, if the contour corresponds to a minimum size and a defined position in the image. The more regular the compactness, the more an inflammation can be anticipated. If this is larger than the compactness of a preceding contour, the average radius R (which results from the distance of each picture point of the contour to the center of gravity $X_K$ of the contour, averaged about the periphery of the contour) will be determined for the current contour. This results in a circle whose center lies in the center of gravity and whose radius=averaged radius (cf. FIG. 17), the surrounding square being defined as a region of interest ROI (cf. FIG. 18).

In this region, the average magenta value and the average saturation value are subsequently determined to assess the segmentation. As a further assessment coefficient, the compactness value is divided by the average radius (since the average size of the filtered area plays a key role for the classification).

At the end of the calculation, three classification values have thus been obtained for a specific threshold. After this, the threshold(mulfactor) is reduced by 1%, and the calculation is started anew. This is done ten times in the first step. In the obtained values, the optimum region for further processing is then taken into consideration, based on the maximum value of these calculations. Unless a suitable result is achieved in the first step, a further reduction of the threshold value is effected in ten steps. The result of the first steps (prefiltering, filtering, calculation of the region of interest—cf. FIG. 18) is a square with a defined starting point and a defined side length in pixels as well as the classification values: average magenta value ($1^{st}$ classification value from segmentation), average saturation value ($2^{nd}$ classification value) and compactness based on radius (kompaktRadius, $3^{rd}$ classification value).

The segmented square is then delivered to the height processing algorithms for further processing and for determining the characteristic values. The sequence of the height determination is illustrated in FIGS. 19 to 22.

Figure 19:
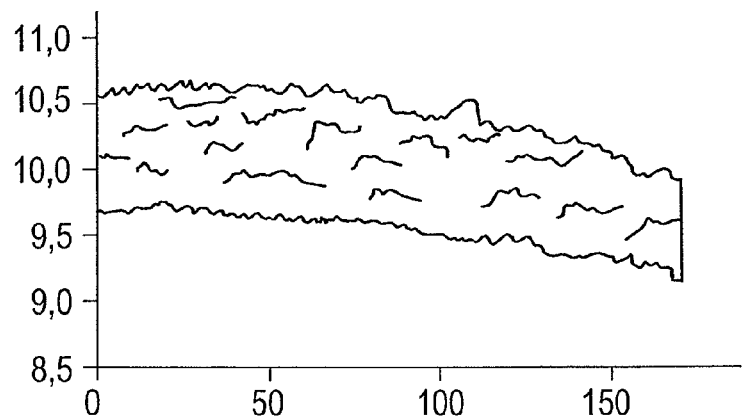
Figure 20:
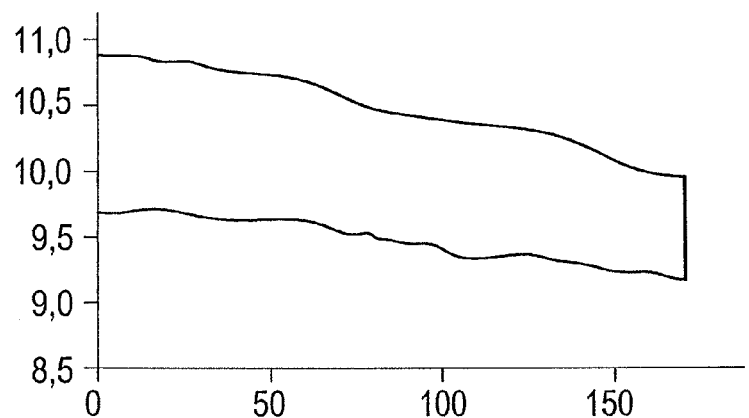
Figure 21:
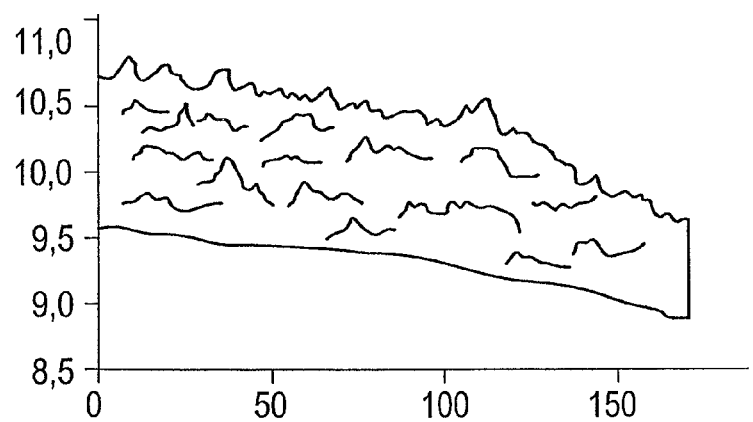
Figure 22:
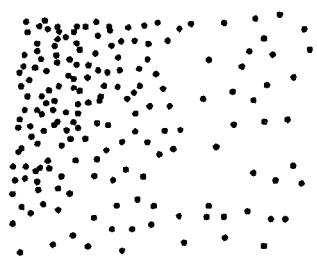

In a first step, a region of interest is established from the original height map that results from the shot taken by the GFM camera (each picture point having its absolute height information, cf. FIG. 19) and filtered. This is done by the aid of a mean value filter, which is applied to the height map until a homogenous surface is formed, which constitutes kind of a mean area for the whole shot (cf. FIG. 20). By the aid of this average area, relative heights of the individual peaks in the height image can then be determined. To this end, a subtraction height map is initially established by subtracting the mean area from the original area (cf. FIG. 21). For all remaining pixels in the image, the relative height is then added, which gives an average volume (=first height classification value·AvgVolume).

In the next step, all peaks (beginning with the highest peak value GH) are searched and reported in a list. If a new peak is traced as the maximum value in the remaining height map, the search will be continued both in the positive and in the negative x and y directions until the pixel values will rise again for the first time. Thus, kind of a summit area will be determined from the summit peak G. The thus obtained surface is deleted from the map to enable a search for the next higher summit. This procedure is repeated until no peaks are traced any more; the heights are stored for all traced peak values, at the end of this procedure the overall height is then divided by the number of traced peaks in order to obtain an average relative height of all peaks in the subtraction height map (=$2^{nd}$ classification value, AvgHeight1).

In order to accelerate further processing, all peaks whose relative heights are below a defined limit value (AvgHeight1*EZThresh) are then filtered out. After this, the third and fourth values can be calculated, AvgArea2 (mean area of remaining peaks) and SumArea1 (base of remaining peaks). In the final step, the maximum height value (i.e. the highest peak in the segmented region) is used to determine the third classification value. In doing so, all remaining peaks whose relative heights are lower than the maximum height by a defined percentage are also filtered out. The remaining highest peaks are then summed up, including their surface areas. Hence result further classification values like the PixelAboveThreshold (base of the then remaining peaks), AvgHeight3 (average height of the then remaining pixels) (cf. FIG. 22).

For the sake of clarity, the performed algorithms are also illustrated in the flow chart according to FIG. 23.

In this respect, it is referred to the following definitions, results, parameters and values, respectively:

AvgMagenta=average magenta value of the pixels inside the contour or the rectangle encompassing the contour AvgSaturation=average saturation value of the pixels inside the contour or the rectangle encompassing the contour kompaktRadius=ratio of the quotient from the surface area and periphery of the contour to the average radius of the contour AvgVolume=average height value of all points having a higher value than the mean value surface area (=volume of addition map)

AvgHeight1=average height of the peaks of all traced peaks

AvgArea2=average area of the peaks whose summits (RelHeight) are above AvgHeight1*EZThresh SumArea1=base (peak area) of those peaks whose summits (RelHeight) are above AvgHeight1*EZThresh AvgHeight 3=average height of those pixels whose height values are larger than PixelAboveThreshThreshold* (height of the highest peak)

PixelAboveThresh=number of pixels above a defined threshold value (as a function of the highest height appearing in the segment)

At the end, the determined values are combined depending on the used camera type for the overall assessment and the determination of comparable classifications, with different combinations and operation variants being possible, e.g. the product of AvgMagenta, AvgSaturation, kompaktRadius, AvgVolume, AvgHeight1 and PixelAboveThreshold or the product of AvgMagenta, AvgSaturation, AvgHeight3, AvgVolume, AvgArea2 and SumArea1. Other combinations are also conceivable. Instead of a multiplication, an addition of the values can also be performed at least partially.

FIG. 14:
S1: Take image
S2: K3ResultData, 400×400
S3: Convert CMYK, HSV
S4: Segment Height
S5: Calc. inflammationVolume
S6: Calc. relVolume
S7: COGinCont=true
S8: Calc. avgMag & avgSat (contour)
S9: Calc. sur_avgMag & sur_avgSat (residual image)
S10: Calc. relMag & relSat
S11: Calc. SK value
S12: Evaluation end (SK value, rel. Mag, rel. Volume)
S13: Calc. avgMag & avgSat (rectangle)
S14: Calc. sur_avgMag & sur_avgSat (residual image)
S41: Calc. polynomial matrix
S42: Calc. polynomial plane
S43: Threshold polynomial plane
S44: Median filter, hair filter (MFO)
S45: Establish height grey image
S46: Segment magenta image
S47: Establish surfaceimg (Magimage+height grey image)
S48: Median filter (9)
S49: Establish binary image by Tresh with avgHeight
S50: Erode (2), dilate (1)
S51: FindContours
S52: MaxAreaContour, boundRect, cog, maxarea
S53: Calc. COG Surfaceimg
S54: COG_s in boundRect
S55: COGinCont=true
S56: Bounding area (red/yellow)
S57: COGinCont=false FIG. 23
T1: Take image
T2: K3ResultData, 400×400
T3: Convert CMYK, HSV
T4: Color segmentation
T5: ROI segment smooth height map
T6: Establish diff. height maps (AvgVolume)
T7: Search maximum (peak, summit) in subtracted map
T8: Determine boundaries and sizes (surface areas) of peaks (AvgHeight1)
T9: List peak properties and "delete" whole peak
T10: Filter out relevant peaks=EZThresh (AvgArea2, SumArea1)
T11: Analyze peaks/pixels via threshold value (PixAbovThreshold) (PixelAboveThresh, AvgHeight 3)
T12: Evaluation end
T41: Prefilter magenta image
T42: Median filter (9)
T43: Erode (2), dilate (1)
T44: Establish binary image
T45: FindContours
T46: kompaktRadius, AvgMag, Avg Sat, ROI
T67: kompaktRadius, AvgMag, Avg Sat, ROI

The invention claimed is:

1. A device for determining a skin inflammation score or value, comprising
an optoelectronic measuring instrument or device for directly taking a three-dimensional image of an inflammation area on human or animal skin, wherein area-related, space and color values of the three-dimensional image are directly detected by the optoelectronic measuring instrument, a processing or computing unit for calculating the skin inflammation score from the area-related, space and color values detected by the measuring instrument, and a display unit for displaying the calculated skin inflammation score, wherein the processing unit distinguishes the area-related values of the scanned three-dimensional image into an inflammation focus and a focus-surrounding area adjoining and surrounding the inflammation focus by delimiting the color values of the individual pixels and by delimiting the space values of the individual pixels and in that each color value corresponds to a magenta value in the CMYK color model;

wherein the scanned three-dimensional image of the inflammation area is comprised of a multitude of pixels arranged in a three-dimensional coordinate system in grid-like fashion, wherein each area-related value corresponds to a single pixel that is unique in the coordinate system;

wherein both a single color value and a single space value are assigned to each area-related value of a three-dimensional image scanned by the optoelectronic measuring instrument;

wherein each space value corresponds to a height value of the respective pixel in the three-dimensional coordinate system;

wherein a relative overall color value of the inflammation focus is determined by comparing the averaged color values in the inflammation focus and the averaged color values in the focus-surrounding area;

wherein the optoelectronic measuring instrument or device is a 3D sensor;

wherein a relative overall volume value of the inflammation focus is determinable by comparing averaged space values in the inflammation focus to averaged space values in the focus-surrounding area;

wherein the relative overall volume value is a comparative value of the surface roughness in the inflammation focus to the surface roughness in the focus-surrounding area.

2. The device according to claim 1, wherein an absolute overall volume value of the inflammation focus is determinable from the space values in the inflammation focus.

3. The device according to claim 1, wherein an area-related value corresponds to a peripheral value corresponding to the periphery of the inflammation focus, and/or an area-related value corresponds to an area value representing the surface area of the inflammation focus.

4. The device according to claim 3, wherein an area-related value is formed as a function of the area value and of the peripheral value and corresponds to a compactness value representing the ratio of the peripheral value to the area value.

5. The device according to claim 1, wherein a relative overall volume value corresponds to an average height value representing the average height of all elevations in the inflammation focus and/or a maximum-height area value representing the surface area of the highest elevations, the highest elevations being those elevations whose heights are at least 70% of the height of the highest elevation.

6. The device according to claim 5, wherein the highest elevations being those elevations whose heights are at least 85% of the height of the highest elevation.

7. A method of evaluating three-dimensional images to be, in particular, performed with a device according to claim 1, comprising an optoelectronic measuring instrument or device a processing or computing unit, and a display unit, characterized by the steps of taking a three-dimensional image of an inflammation area on human or animal skin by the optoelectronic measuring instrument, determining area-related, color and space values of the three-dimensional image, calculating the skin inflammation score or value from the calculated area-related, color and space values, subdividing the inflammation area into an inflammation focus and a focus-surrounding area, wherein the area of the inflammation focus is delimited from the area of the focus-surrounding area by the color and/or space values assigned to the individual area-related values, and displaying the calculated skin inflammation score on the display unit.

8. The method according to claim 7, wherein the further steps of:

assigning each of the determined color values and space values of the surface of the scanned image to a pixel representing the area-related values of the three-dimensional image, said three-dimensional image being composed of a multitude of pixels arranged in grid-like fashion, calculating either an absolute overall color value corresponding to the averaged color value of the inflammation focus, or a relative overall color value corresponding to the averaged color value of the inflammation focus in relation to the averaged color value of the focus-surrounding value, calculating an absolute overall volume values corresponding to the sum of the individual space values of the inflammation focus, and/or a relative overall volume value which is calculated by comparing the individual space values of the inflammation focus to the individual space values of the focus-surrounding area, calculating the skin inflammation score a. from at least one of the calculated overall color values and at least one of the calculated overall volume values, or b. by assigning at least one of the calculated overall color values to a defined inflammation class, assigning at least one of the calculated overall volume values to a defined inflammation class, and forming a mean value from the inflammation classes determined by said assigning, and outputting a rounded mean value as said skin inflammation score.

9. The method according to claim 8, wherein the averaged color value is an averaged magenta value, and the relative overall volume value is a roughness value.

10. The method according to claim 7, wherein the optoelectronic measuring instrument or device is a 3D scanner.

* * * * *